(12) United States Patent
Ikeda

(10) Patent No.: US 6,642,519 B2
(45) Date of Patent: Nov. 4, 2003

(54) FINE PATTERN INSPECTION APPARATUS AND METHOD AND MANAGING APPARATUS AND METHOD OF CRITICAL DIMENSION SCANNING ELECTRON MICROSCOPE DEVICE

(75) Inventor: Takahiro Ikeda, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/254,664

(22) Filed: Sep. 26, 2002

(65) Prior Publication Data

US 2003/0071213 A1 Apr. 17, 2003

(30) Foreign Application Priority Data

Sep. 27, 2001 (JP) ........................................ 2001-296275

(51) Int. Cl.[7] .................... G01N 23/225; G01R 31/305; H01J 37/28
(52) U.S. Cl. ...................... 250/307; 250/306; 250/309; 250/310; 250/399; 257/48; 438/11; 438/14; 438/15; 438/18
(58) Field of Search ................................ 250/306, 307, 250/309, 310, 311, 399; 257/48, 748; 438/11, 14, 15, 18; 356/394; 324/750, 751

(56) References Cited

U.S. PATENT DOCUMENTS

| | | | | |
|---|---|---|---|---|
| 6,576,923 B2 | * | 6/2003 | Satya et al. | 257/48 |
| 6,583,634 B1 | * | 6/2003 | Nozoe et al. | 324/751 |
| 2001/0011706 A1 | * | 8/2001 | Nara et al. | 250/397 |
| 2002/0109088 A1 | * | 8/2002 | Nara et al. | 250/306 |
| 2002/0113967 A1 | * | 8/2002 | Nara et al. | 356/394 |
| 2003/0071213 A1 | * | 4/2003 | Ikeda | 250/307 |
| 2003/0096436 A1 | * | 5/2003 | Satya et al. | 438/11 |

FOREIGN PATENT DOCUMENTS

JP         08-022794         1/1996

OTHER PUBLICATIONS

Archie et al., "Modeling And Experimental Aspects Of Apparent Beam Width As An Edge Resolution Measure", Mar. 1999, SPIE vol. 3677, (pp. 669–685).
Davidson et al., "An Inverse Scattering Approach To SEM Line Width Measurements", Mar. 1999, SPIE vol. 3677 (pp. 640–649).

* cited by examiner

Primary Examiner—John R. Lee
Assistant Examiner—Bernard Souw
(74) Attorney, Agent, or Firm—Finnegan, Henderson, Farabow, Garrett & Dunner, L.L.P.

(57) ABSTRACT

A fine pattern inspection apparatus includes: a first calculation unit which receives data of a first secondary electron signal obtained by irradiating a plurality of test patterns formed on a test substrate with an electron beam and receives data of an contour shape of a cross-section of each of the test patterns, the test substrate being the same as a substrate on which a pattern to be inspected is formed, the test patterns being formed with different cross-sectional shapes, and which separates the first secondary electron signal into variables of a first function containing the contour shape of the cross-section as arguments, a second function that is defined by a step function depending on respective materials constituting the test patterns and a third function that represents the size of a distortion of the signal; a storing unit which has a first storing area to store the first through third functions obtained from the first calculation unit; and a second calculation unit which receives data of a second secondary electron signal obtained by irradiating the pattern to be inspected with an electron beam, and executes calculations so as to extract components relating to the cross-sectional shape of the pattern to be inspected from the second secondary electron signal by using the first through third functions stored in the storing unit.

17 Claims, 14 Drawing Sheets

FINE PATTERN INSPECTION APPARATUS AND METHOD AND MANAGING APPARATUS AND METHOD OF CRITICAL DIMENSION SCANNING ELECTRON MICROSCOPE DEVICE

CROSS REFERENCE TO RELATED APPLICATION

This application claims benefit of priority under 35USC §119 to Japanese patent application No. 2001-296275, filed on Sep. 27, 2001, the contents of which are incorporated by reference herein.

BACKGROUND OF THE INVENTION

1. Field of the Invention

The present invention relates to an inspection apparatus and an inspection method of a fine pattern, and more particularly, it concerns an inspection apparatus and an inspection method of a fine pattern in a semiconductor device manufacturing process as well as a managing apparatus and a managing method of a CD-SEM device.

2. Description of the Prior Art

In semiconductor manufacturing processes, in most cases, a dimension inspection of a fine pattern is carried out by a scanning electron microscope device that is referred to as a CD-SEM (Critical Dimension Scanning Electron Microscope) device.

As shown in FIG. 15A and FIG. 15B, the principle of dimension measurements by a CD-SEM device mainly uses the fact that the intensity of a secondary electron signal varies depending on pattern shapes. Specifically, as shown in FIG. 15A, assuming that the angle made by a primary beam (electron beam) and a normal component of a pattern side wall which is irradiated with this primary beam is θ, the intensity of a secondary electron signal released from the irradiation point is schematically given by a diffusion reflection model of Lanbert represented by the following formula.

$$I = I_o (\cos \theta)^{-n}. \quad \text{[FORMULA 1]}$$

where n represents a diffusion exponent which is a positive number close to 1.

In accordance with this principle, the signal intensity sharply rises in the vicinity of an edge corresponding to a steep portion of a pattern profile. Therefore, in a conventional inspection method of fine patterns using a SEM device, this signal in the vicinity of an edge is analyzed, and the edge position is defined by using a threshold method, for example, peak detection shown in FIG. 15B, function modeling and so forth, so that the pattern dimension is calculated as the distance between edges.

However, the secondary electron signal is subjected to various electrical and numeric modulations due to the following reasons. That is, the primary beam tends to expand, the area from which secondary electrons are discharged tends to expand due to diffusion of electrons emitted from the surface in the vicinity of the irradiation point, the beam scanning signal tends to deviate, the relative position between the pattern and the beam tends to vary in an attempt to improve the SN ratio in accumulation of signals, digital errors occur when the signal is AD-converted, etc. Consequently, in an actual operation, signal from edge portions tend to expand. Moreover, the secondary electron signal is susceptible to influences from distortions in a signal caused by a biased surface electrical potential exerted on the sample surface depending on irradiation conditions of the primary beam and from variation in the secondary electron discharging efficiency based on charging effect of a side wall as well as from contrast resulting from materials such as atomic number, density and dielectric constant. As a result, the signal intensity actually obtained is represented by formula (1) on which these many factors are multiplexed.

These influences make the signal in the vicinity of pattern edge broader, with the result that portions, located outside actual pattern edges by few nm through few tens of nm, might be defined as edges in the conventional edge defining system. Moreover, these influences also tend to vary depending on factors, such as the height and width of a pattern, flat face shape thereof, the relationship between the pattern shape and the scanning direction of primary electrons, the irradiation conditions of the primary beam and the material of the pattern. For these reasons, it has been difficult to precisely compare dimensions among a plurality of patterns.

Here, some techniques which can correct some of the factors that modulate the above-mentioned signals in the vicinity of edges have been proposed.

For example, on page 566 in preliminary report No. 2 in the 39th spring joint seminar associated with applied physics in 1992, a method has been proposed in which the expansion of a primary beam is preliminarily measured so that the expansion component is subjected to a de-convolution process from a line profile. However, this method can only correct the effects of expansion in the primary beam.

Moreover, for example, Proc. SPIE vol. 3677, pp669–685 (1999) has proposed a method in which a signal waveform in the vicinity of an edge of a photoresist pattern having an extremely vertical side-wall shape is obtained by a CD-SEM device so that its half-value width is defined as ABW (Apparent Beam Width). In this document, it is preliminarily examined how the ABW changes depending on the above-mentioned various variation factors. Therefore, in principle, it is possible to obtain positional information corresponding to an actual pattern edge position from a signal waveform of a CD-SEM device by using the results thereof. However, practical solutions to such applications have not been proposed. Moreover, the side wall shape of a sample used for examining the ABW is not completely vertical, the resulting errors are contained in the estimation of the ABW.

Furthermore, pp. 640–649 of the same Proc. SPIE vol. 3677 (1999) have disclosed a method in which the signal waveform is estimated through Monte Carlo simulation based upon information such as the pattern cross-sectional shape, beam conditions of a SEM device and the material of a sample so that the signal transmission function is determined so as to make the waveform coincident with a signal waveform to be actually acquired in a reversed manner, and the components of the signal transmission function are lastly removed from the acquired secondary electron signal for each time so as to estimate the cross-sectional shape of the pattern to be inspected. However, in this method, the Monte Carlo calculation is carried out after a physical model on which the signal waveform is generated is set, therefore, in the case when the adopted model is not established, for example, in such a case when a surface of a pattern is charged, a great error has occurred. Moreover, since the Monte Carlo calculation normally takes a very long processing time, this method fails to provide a practical inspection method.

BRIEF SUMMARY OF THE INVENTION

According to a first aspect of the invention, there is provided a fine pattern inspection apparatus comprising: a first calculation unit which receives data of a first secondary electron signal obtained by irradiating a plurality of test patterns formed on a test substrate with an electron beam and receives data of an contour shape of a cross-section of each of the test patterns, the test substrate being the same as a substrate on which a pattern to be inspected is formed, the test patterns being formed with different cross-sectional shapes, and which separates the first secondary electron signal into variables of a first function containing the contour shape of the cross-section as arguments, a second function that is defined by a step function depending on respective materials constituting the test patterns and a third function that represents the size of a distortion of the signal; a storing unit which has a first storing area to store the first through third functions obtained from the first calculation unit; and a second calculation unit which receives data of a second secondary electron signal obtained by irradiating the pattern to be inspected with an electron beam, and executes calculations so as to extract components relating to the cross-sectional shape of the pattern to be inspected from the second secondary electron signal by using the first through third functions stored in the storing unit.

According to a second aspect of the invention, there is provided an apparatus connectable to CD-SEM devices and which manages the CD-SEM devices, the managing apparatus comprising: a calculation unit which receives data of a secondary electron signal from a plurality of different CD-SEM devices and receives data of an contour shape of a cross-section of each of the test patterns, the secondary electron signal being obtained by irradiating a plurality of test patterns formed on a test substrate with an electron beam, the test substrate being the same as a substrate on which a pattern to be inspected is formed, the test pattern being formed with different cross-sectional shapes, and which separates the secondary electron signal into variables of a first function containing the contour shape of the cross-section as arguments, a second function that is defined by a step function depending on respective materials constituting the test patterns and a third function that represents the size of a distortion of the signal, for each of the CD-SEM devices; a storing unit which stores the first function obtained from the calculation unit for each of the CD-SEM devices; and a monitoring unit which monitors performance differences among the CD-SEM devices by mutually comparing the first functions among the CD-SEM devices.

According to a third aspect of the invention, there is provided an apparatus connectable to a CD-SEM device and which manages the CD-SEM device, the managing apparatus comprising: a calculation unit which receives data of a secondary electron signal from the CD-SEM device at different times and receives data of an contour shape of a cross-section of each of the test patterns, the secondary electron signal being obtained by irradiating a plurality of test patterns with an electron beam, the test patterns being formed on a substrate with different cross-sectional shapes, and which separates the secondary electron signal into variables of a first function containing the contour shape of the cross-section as arguments, a second function that is defined by a step function depending on respective materials constituting the test patterns and a third function that represents the size of a distortion of the signal, at each of the times; a storing unit which stores the first function obtained from the calculation unit in association with each of the times; and a monitoring unit which monitors time-based variations in the CD-SEM devices by mutually comparing the first functions among the times.

According to a fourth aspect of the invention, there is provided a fine pattern inspection method comprising: acquiring data of a first secondary electron signal obtained by irradiating a plurality of test patterns formed on a test substrate with an electron beam, the test substrate being the same as a substrate on which a pattern to be inspected is formed, the test patterns being formed with different cross-sectional shapes, and acquiring data of an contour shape of a cross-section of each of the test patterns; separating the first secondary electron signal into variables of a first function containing the contour shape of the cross-section as arguments, a second function that is defined by a step function depending on respective materials constituting the test patterns and a third function that represents the size of a distortion of the signal; recording the first through third functions obtained from the separation of variables; acquiring data of a second secondary electron signal obtained by irradiating the pattern to be inspected with an electron beam; and executing calculations so as to extract components relating to the cross-sectional shape of the pattern to be inspected from the second secondary electron signal by using the first through third functions that have been recorded.

According to a fifth aspect of the invention, there is provided a managing method of a CD-SEM device comprising: acquiring data of a secondary electron signal from a plurality of different CD-SEM devices, the secondary electron signal being obtained by irradiating a plurality of test patterns with an electron beam, the test patterns being formed on a substrate with different cross-sectional shapes; acquiring data of an contour shape of a cross-section of each of the test patterns; separating the secondary electron signal into variables of a first function containing the contour shape of the cross-section as arguments, a second function that is defined by a step function depending on respective materials constituting the test patterns and a third function that represents the size of a distortion of the signal, for each of the CD-SEM devices; recording the first function for each of the CD-SEM devices; and monitoring performance differences among the CD-SEM devices by mutually comparing the first functions among the CD-SEM devices.

According to a sixth aspect of the invention, there is provided a managing method of a CD-SEM device comprising: acquiring data of a secondary electron signal from the CD-SEM device at different times, the secondary electron signal being obtained by irradiating a plurality of test patterns with an electron beam, the test patterns being formed on a substrate with different cross-sectional shapes; acquiring data of an contour shape of a cross-section of each of the test patterns; separating the secondary electron signal into variables of a first function containing the contour shape of the cross-section as arguments, a second function that is defined by a step function depending on respective materials constituting the test patterns and a third function that represents the size of a distortion of the signal, at each of the times; recording the first function obtained from the separation of variables in association with each of the times; and monitoring time-based variations in the CD-SEM devices by mutually comparing the first functions among the times.

According to a seventh aspect of the invention, there is provided a program which allows a computer to execute a fine pattern inspection method comprising: acquiring data of a first secondary electron signal obtained by irradiating a plurality of test patterns formed on a test substrate with an electron beam, the test substrate being the same as a substrate on which a pattern to be inspected is formed, the test patterns being formed with different cross-sectional shapes, and acquiring data of an contour shape of a cross-section of each of the test patterns; separating the first secondary electron signal into variables of a first function containing the contour shape of the cross-section as arguments, a second function that is defined by a step function depending on respective materials constituting the test patterns and a third function that represents the size of a distortion of the signal; recording the first through third functions obtained from the separation of variables; acquiring data of a second secondary electron signal obtained by irradiating the pattern to be inspected with an electron beam; and executing calculations so as to extract components relating to the cross-sectional shape of the pattern to be inspected from the second secondary electron signal by using the first through third functions that have been recorded.

According to an eighth aspect of the invention, there is provided a program which allows a computer to execute a managing method of a CD-SEM device comprising: acquiring data of a secondary electron signal from a plurality of different CD-SEM devices, the secondary electron signal being obtained by irradiating a plurality of test patterns with an electron beam, the test patterns being formed on a substrate with different cross-sectional shapes; acquiring data of an contour shape of a cross-section of each of the test patterns; separating the secondary electron signal into variables of a first function containing the contour shape of the cross-section as arguments, a second function that is defined by a step function depending on respective materials constituting the test patterns and a third function that represents the size of a distortion of the signal, for each of the CD-SEM devices; recording the first function for each of the CD-SEM devices; and monitoring performance differences among the CD-SEM devices by mutually comparing the first functions among the CD-SEM devices.

According to a ninth aspect of the invention, there is provided a program which allows a computer to execute a managing method of a CD-SEM device comprising: acquiring data of a secondary electron signal from the CD-SEM device at different times, the secondary electron signal being obtained by irradiating a plurality of test patterns with an electron beam, the test patterns being formed on a substrate with different cross-sectional shapes; acquiring data of an contour shape of a cross-section of each of the test patterns; separating the secondary electron signal into variables of a first function containing the contour shape of the cross-section as arguments, a second function that is defined by a step function depending on respective materials constituting the test patterns and a third function that represents the size of a distortion of the signal, at each of the times; recording the first function obtained from the separation of variables in association with each of the times; and monitoring time-based variations in the CD-SEM devices by mutually comparing the first functions among the times.

DETAILED DESCRIPTION OF THE INVENTION

Figure 1:
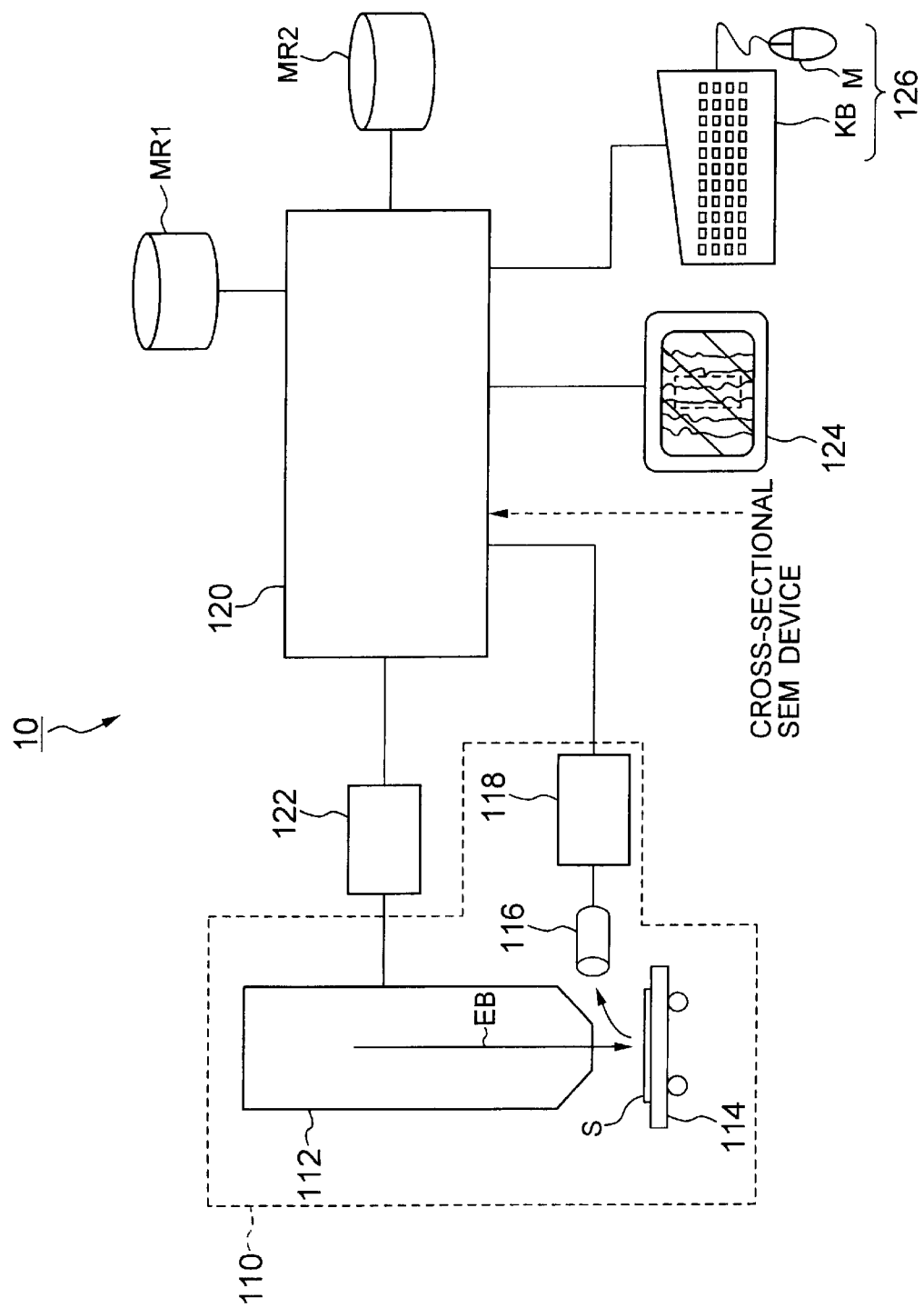
FIG. 1 is a block diagram that includes a first embodiment of a fine pattern inspection apparatus in accordance with the present invention.

Referring now to Figures, the following description will discuss embodiments of the present invention. Here, in the respective drawings, the same parts are denoted by the same reference numerals, and repetitive description thereof is omitted.

(1) First Embodiment of a Fine Pattern Inspection Apparatus

FIG. 1 is a block diagram that shows a first embodiment of a fine pattern inspection apparatus of the present invention together with a CD-SEM device which is connected thereto. A fine pattern inspection apparatus 10, shown in this Figure, comprises an electronic optical system control unit 122, a computer 120, memories MR1, MR2, a display unit 124 and an input unit 126.

The CD-SEM device 110, also shown in FIG. 1, includes a stage 114 on which a substrate S is mounted, an electronic optical system 112, a secondary electron detector 116 and a signal processing unit 118. The electronic optical system 112 generates an electron beam EB to irradiate the substrate S having a fine pattern to be inspected formed thereon, with the electron beam EB. The secondary electron detector 116 detects secondary electrons/reflected electrons/back scattered electrons, which are discharged from the surface of the substrate S due to the irradiation of the electron beam EB. The signal processing unit 118 converts an analog image signal made from the secondary electrons/reflected electrons/back scattered electrons detected by the secondary electron detector 116 to a digital signal, and amplifies this digital signal to supply it to the computer 120 as a secondary electron signal.

The computer 120 controls the entire device in accordance with recipe files stored in the memory MR1. The computer 120 is connected to an electronic optical system 112 of a CD-SEM device 110 via the electronic optical system control unit 122 so as to supply a control signal to the electronic optical signal control unit 122, and is also connected to a signal processing unit 118 of the CD-SEM device 110 so as to receive a secondary electron signal supplied from the signal processing unit 118. Further, the computer 120 is also connected to a cross-section SEM device so that it processes cross-sectional shape data of the pattern that is supplied from this cross-section SEM device, calculates the dimension of the pattern to be inspected through a sequence that will be described later, and/or calculates various amounts of features of the three-dimensional shape thereof.

The display unit 124, which is connected to the computer 120, displays the processing state on demand.

The input unit 126, which includes a keyboard KB and a mouse M, is connected to the computer 120, and supplies various input signals thereto through operations by an operator.

With respect to more specific operations of the fine pattern inspection apparatus 10 shown in FIG. 1, the following description will discuss some embodiments of a fine pattern inspection method in accordance with the present invention.

(2) First Embodiment of a Fine Pattern Inspection Method

Figure 2:
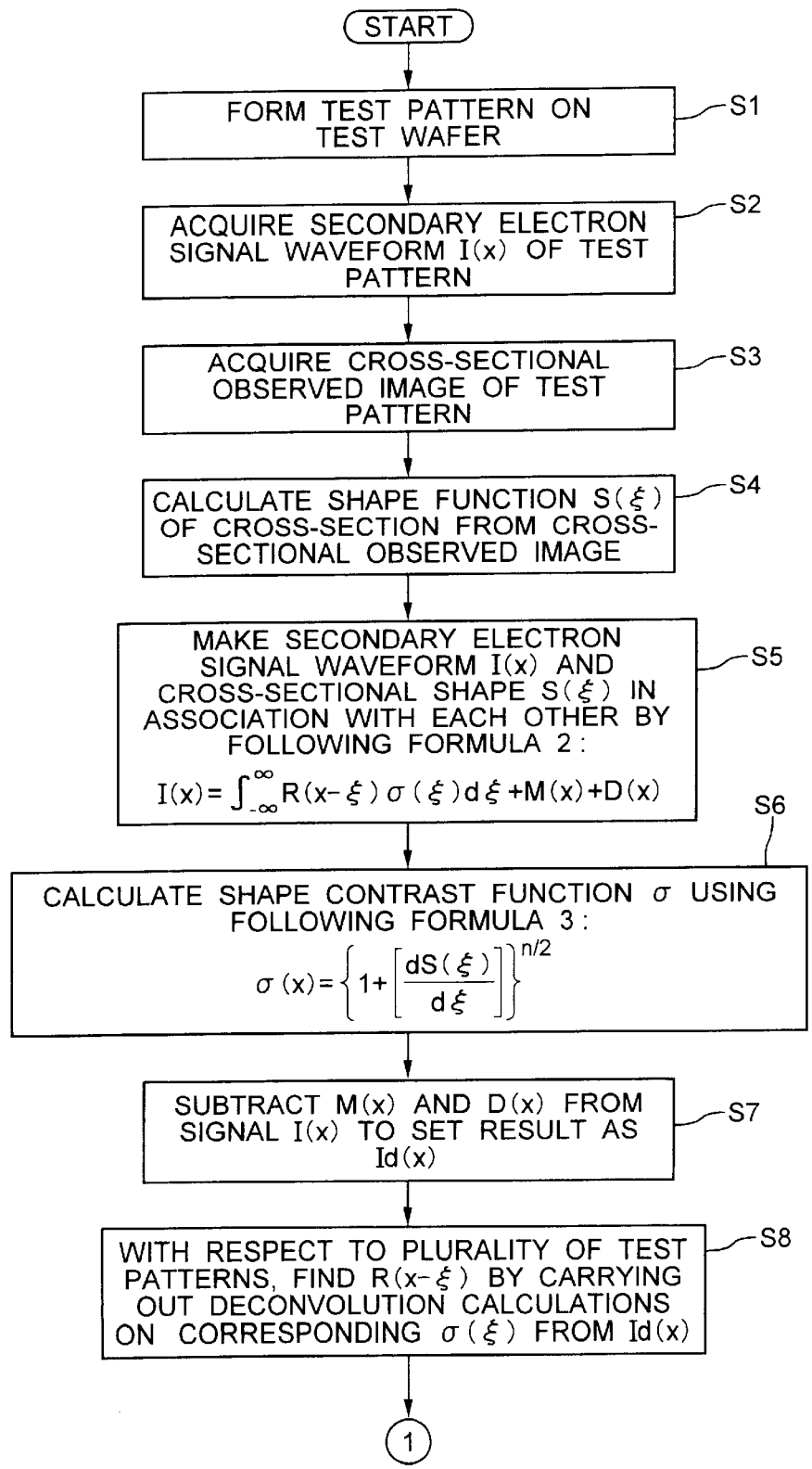
FIGS. 2 and 3 are flow charts that show a schematic sequence of a first embodiment of the fine pattern inspection apparatus in accordance with the present invention.
Figure 3:
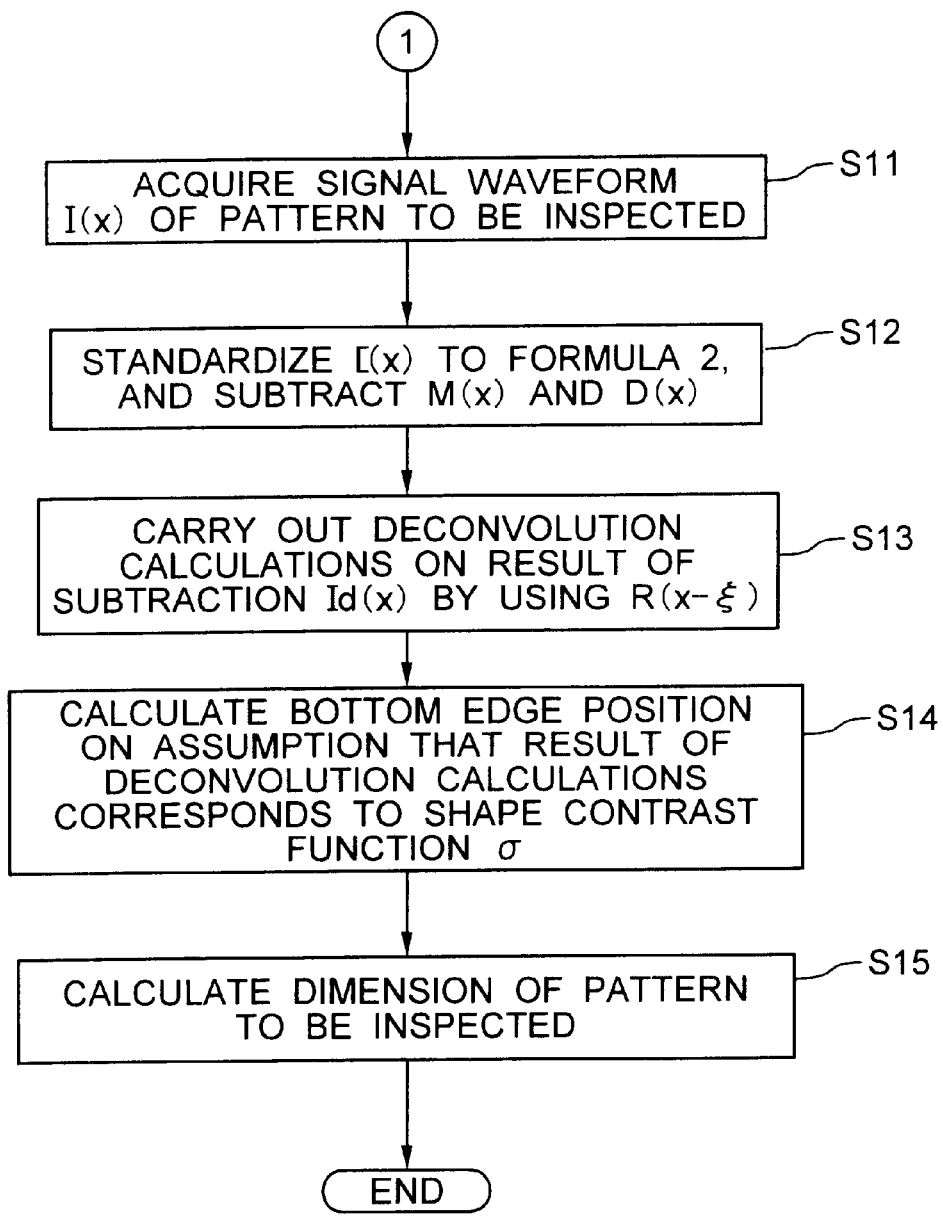
Figure 4A:
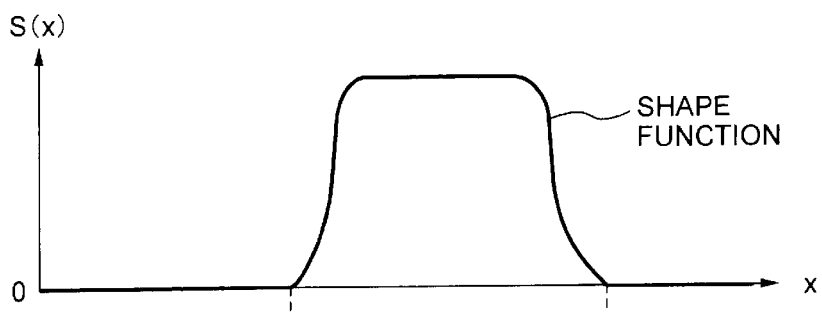
FIG. 4A is a graph that shows a shape function that represents a cross-sectional shape of one example of a pattern to be inspected.
Figure 4B:
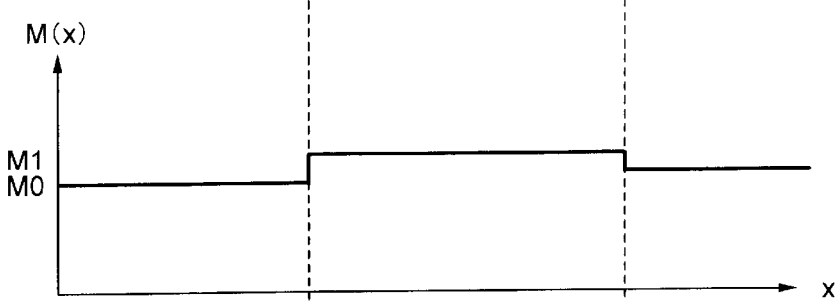
FIG. 4B is a graph that shows a material function of the pattern to be inspected of FIG. 4A.
Figure 4C:
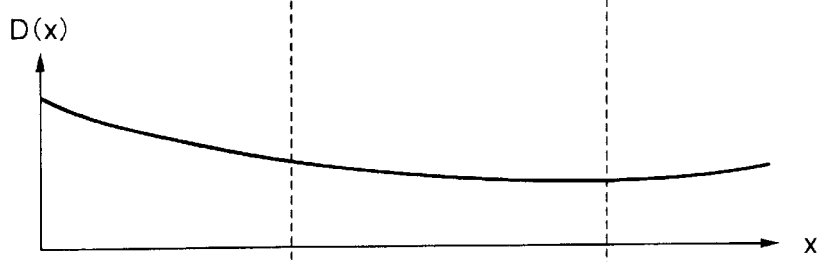
FIG. 4C is a graph that shows a signal distortion function.
Figure 4D:
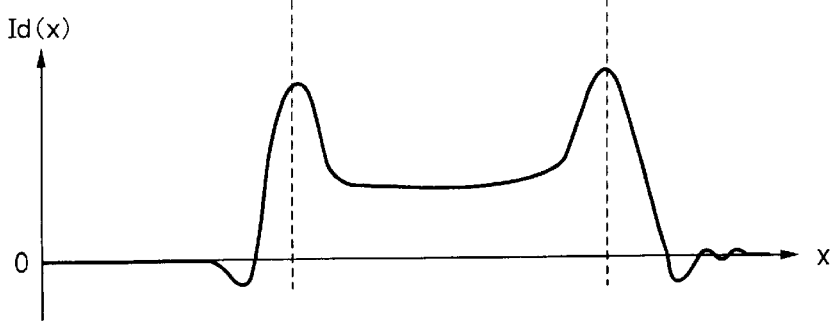
FIG. 4D is a graph that shows results obtained by subtracting each of components of the material function shown in FIG. 4B and the signal distortion function shown in FIG. 4C from a secondary electron signal waveform obtained from a CD-SEM device.
Figure 5:
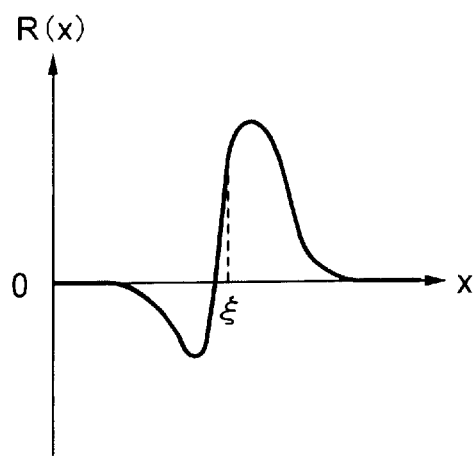
FIG. 5 is a drawing that explains a shape response function that makes a secondary electron signal waveform and a shape function associated with each other.

FIG. 2 and FIG. 3 show a flow chart that indicates a schematic sequence of a fine pattern inspection method of the present embodiment, and FIG. 4A through FIG. 5 are explanatory drawings that show the fine pattern inspection method shown in FIG. 2 and FIG. 3.

First, prior to the actual inspection of a pattern to be inspected, a test wafer on which a test pattern is formed is prepared (step S1). For the test wafer, the same substrate as a substrate on which the pattern to be inspected is actually formed is used. In the present embodiment, a substrate coated with an anti-reflective layer of 100 nm is used. The test pattern is formed on the test wafer in a state in which some process variations are intentionally applied to the same pattern as the pattern to be inspected.

More specifically, using a photomask on which a test pattern is arranged, which totally includes all the combinations among the pattern width to which the forming process of the pattern to be inspected is applied, the direction on wafer coordinates of the pattern to be inspected and the pattern pitches to be applied, the test pattern is imaged onto the test wafer while the set focus value and set exposure amount of a light exposure device are varied for every shot. In the present embodiment, line patterns are imaged as the test pattern, which has line widths of three standards of approximately 0.13 µm, approximately 0.15 µm and approximately 0.2 µm, with pattern pitches, that is, ratios between the line width and widths of spaces between the lines, being set to 1:1, 1:1.5, 1:3 and 1:10. The line patterns are formed so as to be capable of being placed in both of the lateral direction (X direction) and the longitudinal direction (Y direction) when the wafer notch faces down. Next, using a photomask on which 24 types of test patterns including all the combinations are arranged, the test pattern are imaged on the wafer. In exposure, the focusing process is intentionally varied by 0.1 µm shift from the best focus value of the exposing device as the center for every exposing shot. Moreover, about the amount of exposure in which the line pattern of 0.13 µm with the ratio of line width:space width of 1:1 is formed in substantial success, as the center, the amount of exposure is also intentionally varied by 2.5% shift of the amount of exposure for every exposing shot.

Next, the test wafer formed as described above is loaded into the CD-SEM device 110 (see FIG. 1) of the fine pattern inspection apparatus 10, and with respect to all the test patterns of all the exposing shots, data of the secondary electron signal I(x), obtained through CD-SEM observations, is acquired (step S2 in FIG. 2).

Then, the above-mentioned test wafer is taken out of the CD-SEM device 110, and all the test patterns at all the test shots are subjected to cleavage in a direction orthogonal to the longitudinal direction thereof, and loaded into a cross-section SEM device, and cross-sectional observed images are respectively acquired with respect to all the test patterns at all the exposing shots (step S3).

Then, the cross-sectional observed images thus acquired are subjected to a binarization process, image pixel coordinates corresponding to a border between black and white are acquired as numeric data of the contour of a cross-section, and the result thereof is defined to a function S(ξ) (step S4). FIG. 4A shows one example of this cross-sectional shape function.

Next, the secondary electron signal waveform I(x) acquired at step S2, and the cross-sectional shape S(ξ) acquired at the above-mentioned step S4 are associated with each other so that the relationship between the two is standardized by the following formula by using a shape response function R, a material function M(x) and a signal distortion function D(x)(step S5).

$$I(x) = \int_{-\infty}^{\infty} R(x-\xi)\sigma(\xi)d\xi + M(x) + D(x) \quad \text{[FORMULA 2]}$$

where σ(ξ) is a shape contrast function corresponding to $(\cos\theta)^{-n}$ of formula 1, and is made in association with the shape function S(x) by the relationship expressed by the following formula:

$$\sigma(x) = \left\{1 + \left[\frac{dS\xi}{d\xi}\right]\right\}^{n/2} \quad \text{[FORMULA 3]}$$

Here, n is a diffusion exponent in the aforementioned Lanbert's law, and this exponent can be regarded as 1 in most cases. Therefore, in the following sequence, on the assumption that this exponent is equal to 1, σ(x) is found from the above-mentioned S(ξ) (step S6).

The material function M(x) is given as a stepped function shown in FIG. 4B depending a layered structure constituting the pattern. In other words, in a portion where resist is present, the size is set to M1, and in a portion where no resist is present, the size is set to M0.

Figure 15A:
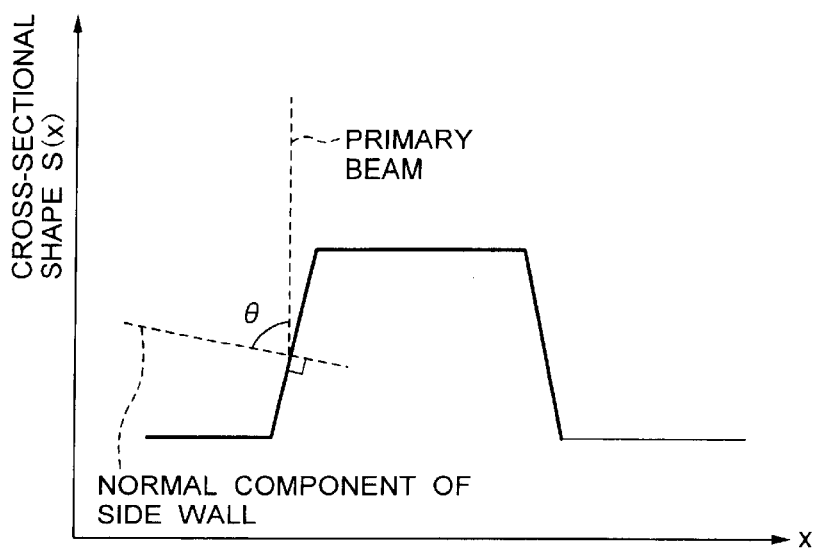
FIGS. 15A and 15B are drawings that explain the principle of pattern dimension measurements in accordance with a conventional technique.
Figure 15B:
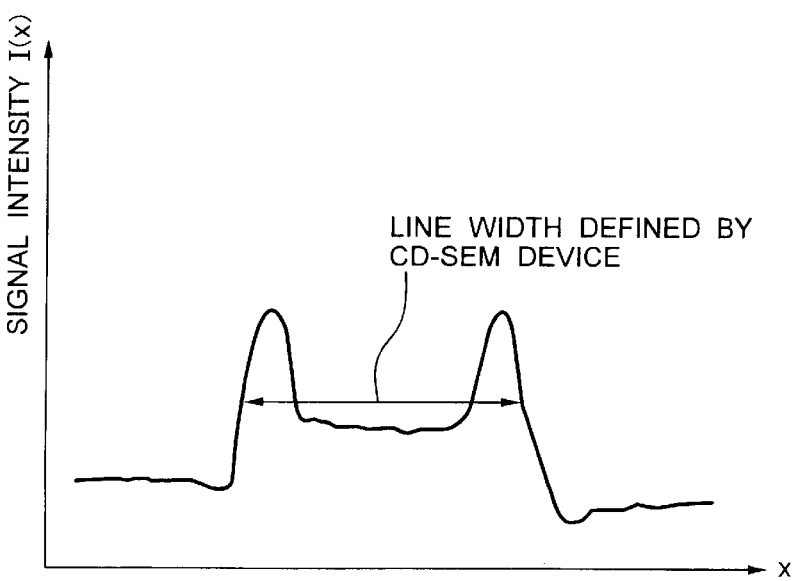

Moreover, the signal distortion function D(x) is a function of the shape function S(x), and set so as to be determined for every material forming the pattern to be evaluated and for every observation condition of the CD-SEM device 110. FIG. 4C shows a signal distortion function D(x) that corresponds to the shape function S(x) shown in FIG. 4A. Here, the observation conditions of the CD-SEM device 110 include the beam scanning frequency, observing magnification, sampling current, signal acquiring time, number of signal accumulations, angle of a beam scanning direction with respect to the pattern edge direction (see FIG. 15A), position of a pattern to be inspected in a scanning area, etc.

In the present embodiment, D(x) is represented by the following formula:

$$D=(x)=d_0+d_1x+d_2x^2 \quad \text{[FORMULA 4]}$$

Next, with respect to the secondary electron signal waveform I(x) obtained by the CD-SEM device 110 for the test patterns corresponding to various focuses and amounts of dose, components other than those in the vicinity of edges are examined so that a function form among values of M0, M1 and D(x) is obtained through a least square method.

As a result, in the present embodiment, it is found that M1 and M0 may be set as the same value since substances of M1 and M0 are mutually similar to a great extent. Thus, this value is set to a constant M.

The respective components σ(x), M(x) and D(x), obtained through the above-mentioned sequence, are stored in the memory MR2 (see FIG. 1).

Next, components of M(x) and D(x) are subtracted from the signal I(x) so that the result is set to Id(x) (step S7, in FIG. 2). FIG. 4D shows one example of Id(x).

Next, numerical de-convolution calculations are carried out from the Id(x) obtained from various signals to the corresponding σ(ξ), and these de-convolution calculations are further carried out on patterns having various shapes with varied focuses and dose amounts so that the results are added and averaged to find R(x−ξ). The result of the calculation is then stored in the memory MR2 (step S8). Here, the de-convolution calculations are easily executed through calculations using matrixes, for example, as shown in chapter 7 of "Waveform Data Processing for Scientific Measurements (written by Shigeo Minami, 1986)" published by CQ publishing Co., Ltd.

Through the above-mentioned sequences, all the signal response functions have been determined. Here, as shown in FIG. 5, the shape response function R forms a function having a peak in the vicinity of the edge with its half-value width of approximately 8 nm.

Next, the edge position of a pattern to be inspected is calculated through the following sequence by using the respective functions calculated through the above-mentioned sequences (FIG. 3).

In specific, the signal waveform I(x) of a line pattern to be inspected is acquired under the same signal acquiring conditions as the sequence shown in FIG. 2 (step S11).

Next, the secondary electron signal I(x) is standardized in accordance with formula 2 so that respective components of M(x) and D(x) are taken from the memory MR2, and M(x) and D(x) are subtracted from the standardized I(x)(step S12).

Next, the component of the known shape response function R(x−ξ) is drawn from the memory MR2, and de-convolution calculations are carried out on the result that has been obtained through subtractions in the sequence of step S12 by using the shape response function R(x−ξ) (step S13). These calculations are also executed in the same method as described above.

Next, on the assumption that the result of the deconvolution calculations is a shape contrast function σ, positions corresponding to the pattern edge positions are calculated (step S14).

Lastly, the distance between the pattern edge positions obtained from the above-mentioned sequence is calculated as a pattern dimension (step S15).

Figure 6:
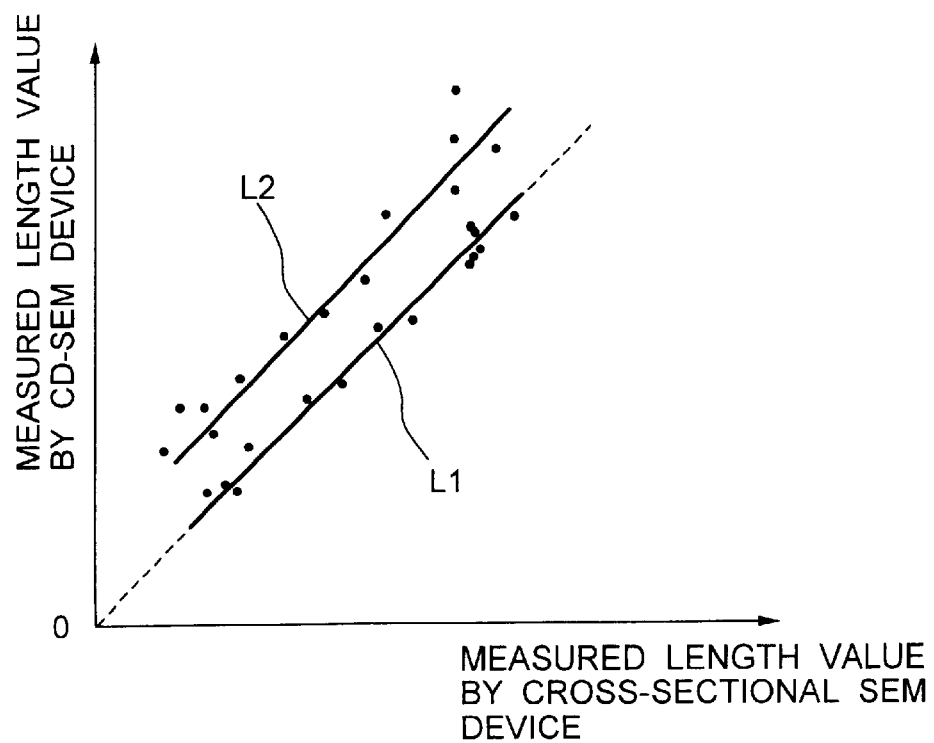
FIG. 6 is a graph that shows the effects of a fine pattern inspection method shown in FIGS. 2 and 3 in comparison with a conventional technique.

After dimension measurements have been carried out on the wafer on which the pattern to be inspected is formed through the above-mentioned sequences, this pattern to be inspected is again subjected to a cross-sectional observation, and comparisons are made among the pattern dimension obtained as a result of the cross-sectional observation, the results of measurements by the present embodiment and the results of measurements calculated through the conventional threshold value method. FIG. 6 shows one example of the result of comparisons. In this Figure, straight line L1 represents the result of measurements in accordance with the present embodiment, and straight line L2 represents the result of measurements in accordance with the conventional threshold value method. In the threshold value method, the threshold value of 50% is adopted. As shown in FIG. 6, it has been confirmed that the inspection method of the present embodiment provides an inspection result closer to the result obtained through the cross-sectional observations irrespective of pattern shapes and pattern pitches.

Here, in the present embodiment, the cross-sectional observation of the pattern is executed by a SEM device used for cross-sectional observation of a pattern, and information of the pattern shape is obtained from the result. However, this process may be carried out by using another method selected by the operator who carries out evaluation depending on respective applications. For example, not a SEM device used for cross-sectional observation, but for example, a CD-SEM device which has a modified wafer tray so as to carry a sample after having been subjected to cleavage, maybe used. Moreover, in the case of measurements with high precision that require edge information with high resolution, it is possible to carry out the cross-sectional observation by using a TEM (Transmission Electron Microscope). Furthermore, in the case when the cross-sectional shape of the pattern is greatly varied depending on processes but high edge resolution is not required in the required specification, profile data obtained by AFM (Atomic Force Microscope) may be utilized without subjecting to the cross-section to cleavage.

Moreover, in the present embodiment, as shown in formula 2, the secondary electron signal is represented by linear connection of a component resulting from a shape, a component resulting from a material and a component resulting from waveform distortion. However, the linear connection is not necessarily used. For example, this may be represented by a product of these three components, and in this case, by taking a logarithm of a signal represented by the product of the three components, it is possible to reach the addition of the above-mentioned three components as is aforementioned in the present embodiment.

In this manner, one of the features of the present embodiment is that a function form which can be separated into variables representing the component resulting from a shape, the component resulting from a material and the component resulting from a signal distortion is adopted as a model of a signal waveform. Thus, the present embodiment makes it possible to carry out an inspection process on a fine pattern at high speeds with high precision.

In the present embodiment, for conversion of a cross-sectional shape into numeric values the cross-sectional observed image is obtained through a binarization process. However, the present invention should not be limited by this method. In other words, in the same manner as the method used in a CD-SEM device, the contour data of a cross-section may be acquired from the results of a threshold value process that is carried out based upon the density of the image, or the cross-sectional image data may be converted into numeric values by using a digitizer through a manual assist. With respect to this point, the same is true to a TEM image. In the case of the application of an AFM this data may be used as it is since the profile data is originally obtained as a numeric data.

(3) Second Embodiment of a Fine Pattern Inspection Method

Next, referring to FIGS. 7 through 9C, the following description will discuss a second embodiment of a fine pattern inspection method in accordance with the present invention.

Figure 7:
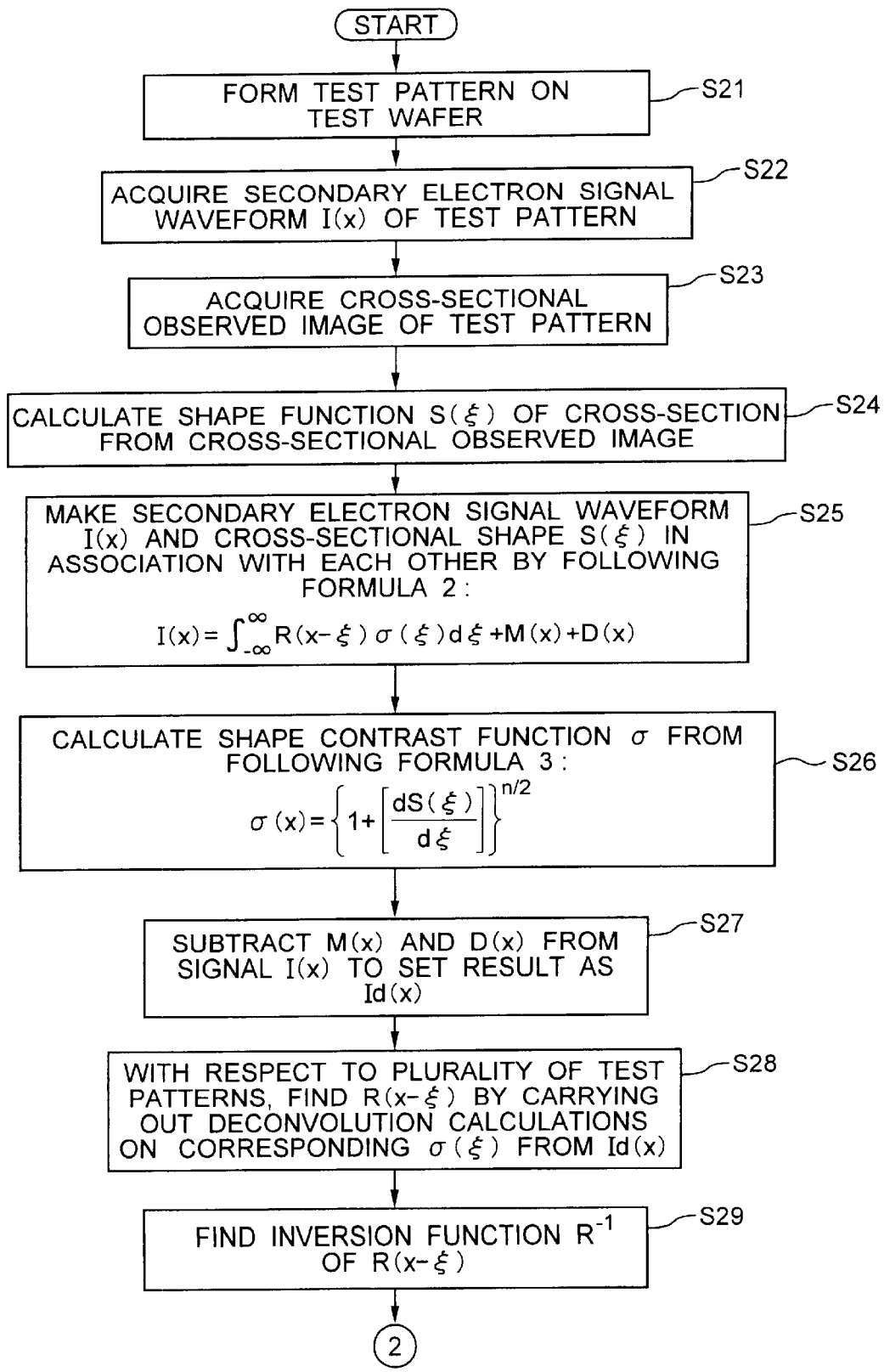
FIGS. 7 and 8 are flow charts that show a schematic sequence of a second embodiment of the fine pattern inspection method in accordance with the present invention.
Figure 8:
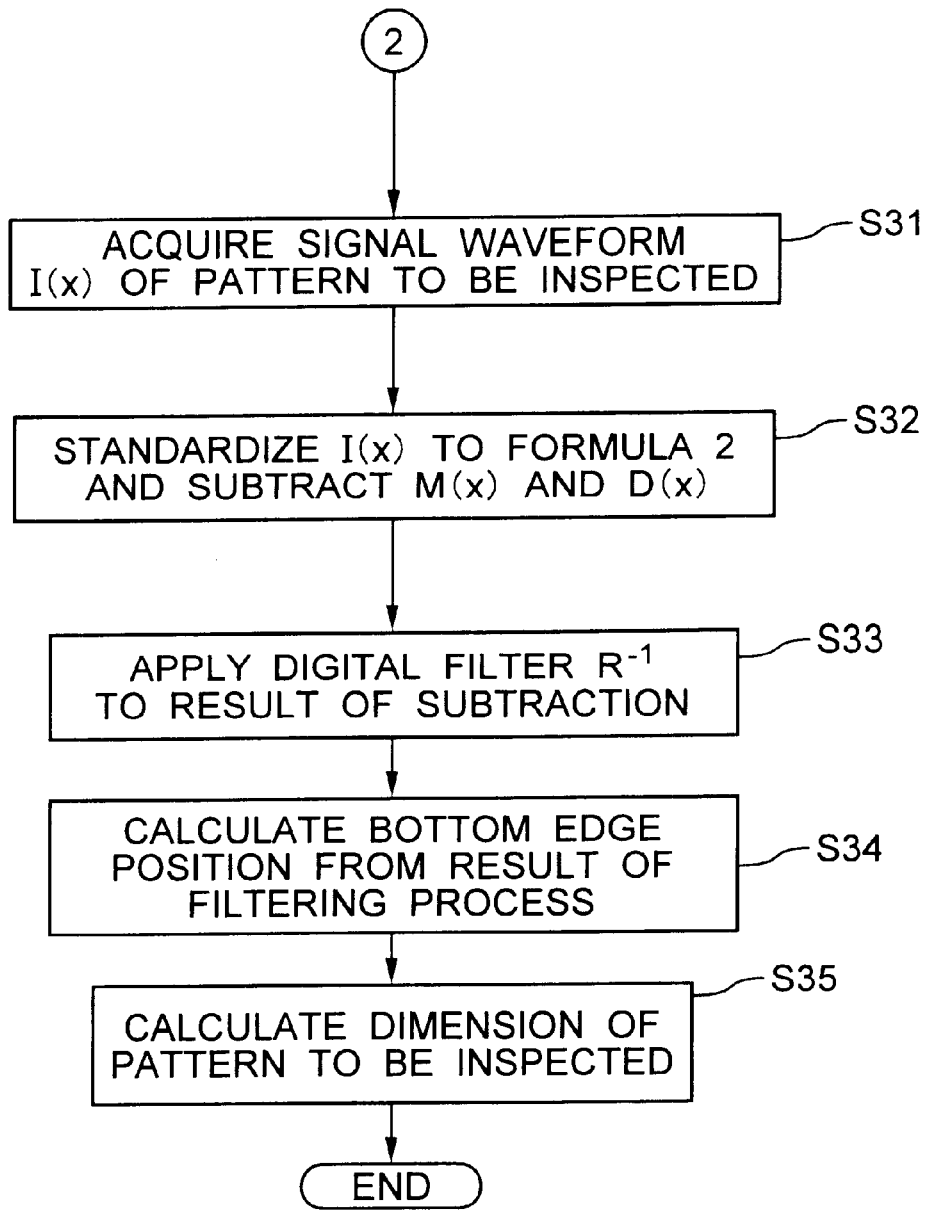

FIG. 7 and FIG. 8 show a flow chart that indicates a schematic sequence of a fine pattern inspection method of the present embodiment, and FIG. 9 is an explanatory drawing that shows the fine pattern inspection method shown in FIG. 7 and FIG. 8.

As clearly be seen by comparison with FIG. 2, the sequence of steps S21 through S28 in the flow chart of FIG. 7, from the step of formation of a test wafer to the step of obtaining of a signal response function, is substantially the same as that of the first embodiment, and each of the numbers of the steps corresponds to that added by 20. Therefore, in the following description, an explanation will start at step S29 that is a featured sequence of the present embodiment.

Figure 9A:
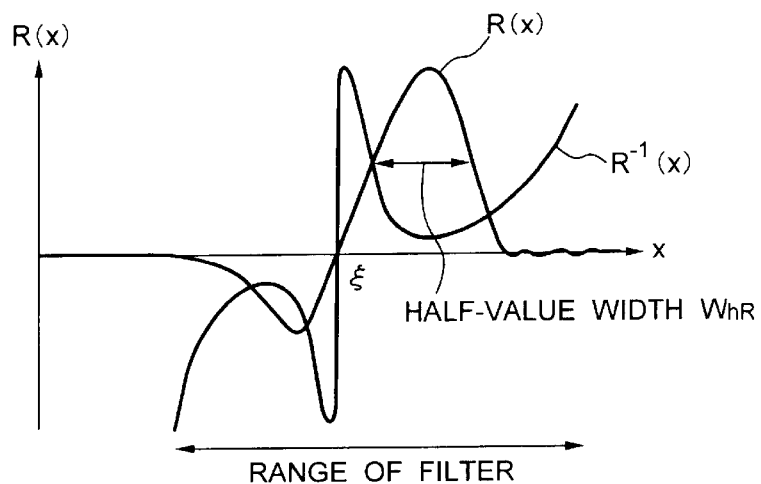
FIGS. 9A through 9C are explanatory drawings that show the fine pattern inspection method of FIGS. 7 and 8.

In specific, after finding the signal response function $R(x-\xi)$ at step S28, an inversion function $R^{-1}$ of $R(x-\xi)$ is numerically found and is stored in the memory MR2 as discrete data (step S29). FIG. 9A shows one example of $R(x-\xi)$ and its inversion function $R^{-1}$.

Here, the inversion function $R^{-1}$ can be regarded as a kind of digital filter. The influences of this filter become smaller as the target position is located farther from the pattern edge. Therefore, as shown in FIG. 9A, in the present embodiment, the range (size) of the filter is set to 5 times greater than the half-value width $W_{hR}$ of R, with the other components being set to 0.

Figure 9B:
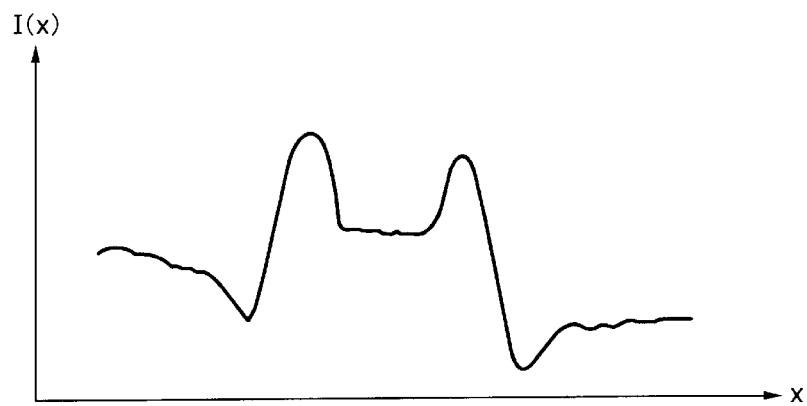

Thereafter, as shown in FIG. 8, after the material function M(x) and the signal distortion function D(x) are subtracted from the signal waveform I(x) acquired from the CD-SEM device 110 (step S31, S32), the above-mentioned filter $R^{-1}$ is applied thereto (step S33). As a result, a curve shown in FIG. 9B is obtained.

Figure 9C:
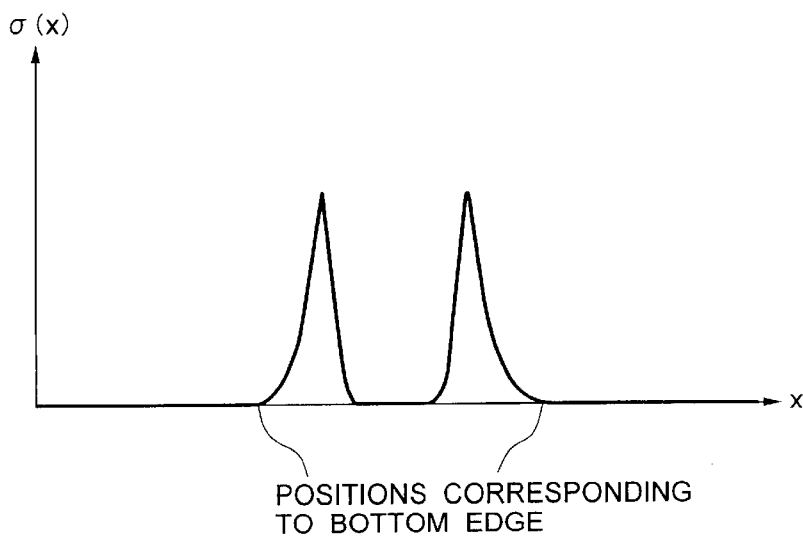

Lastly, as shown in FIG. 9C, the positions corresponding to the bottom edges of the pattern to be inspected are numerically calculated from the results of this filtering process (step S34), distance between the calculated positions is then calculated and the result of the calculation for the distance is defined as a pattern dimension (step S35).

In this manner, in accordance with the present embodiment, a filtering process, which is easily used in a digital waveform process of a signal, is executed so that dimension measurements which have a higher correlation with the results of cross-sectional observation than the conventional technique can be carried out at higher speeds than the aforementioned first embodiment.

(4) Third Embodiment of a Fine Pattern Inspection Method

Figure 10:
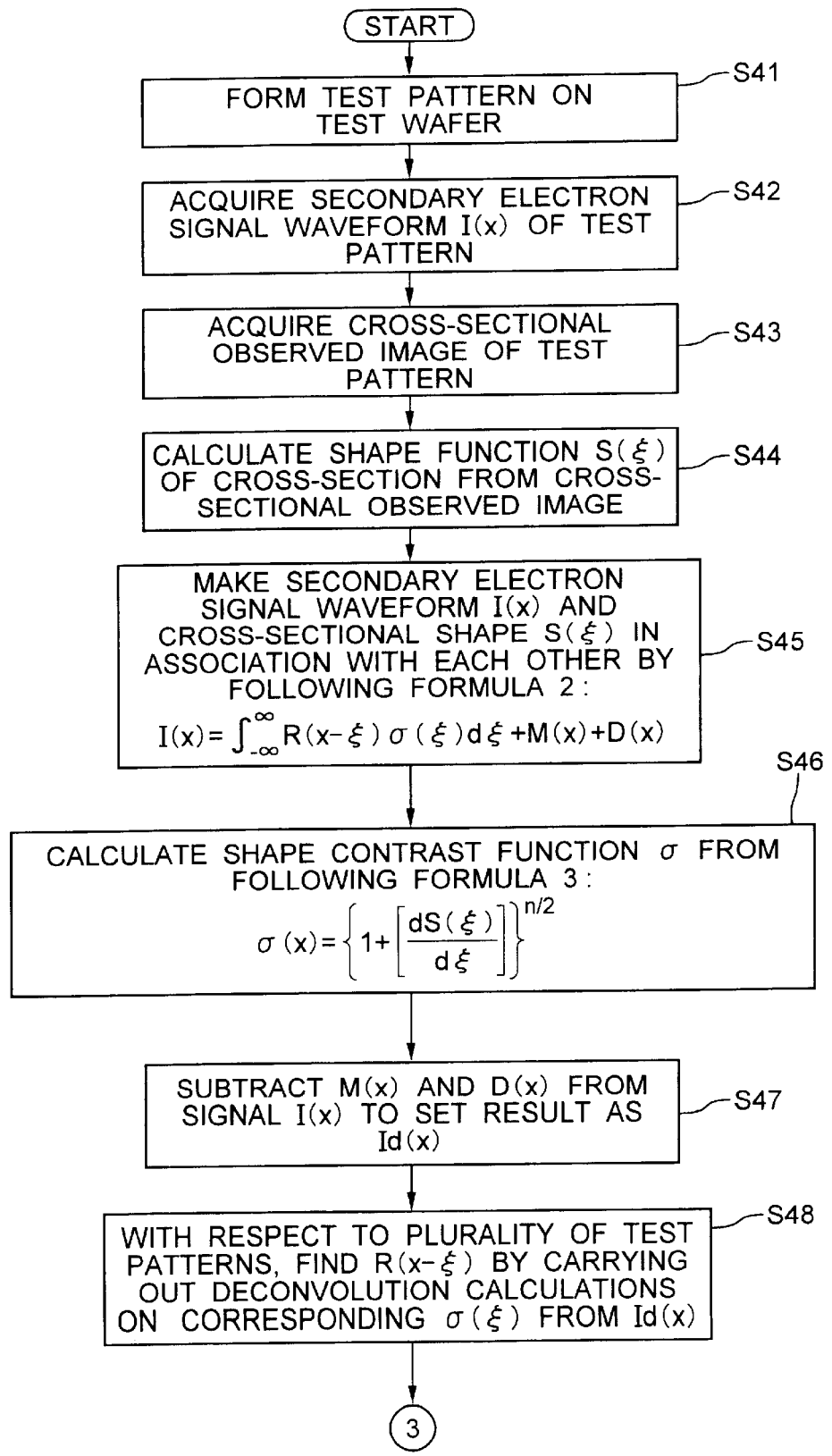
FIGS. 10 and 11 are flow charts that show a schematic sequence of a third embodiment of the fine pattern inspection method in accordance with the present invention.
Figure 11:
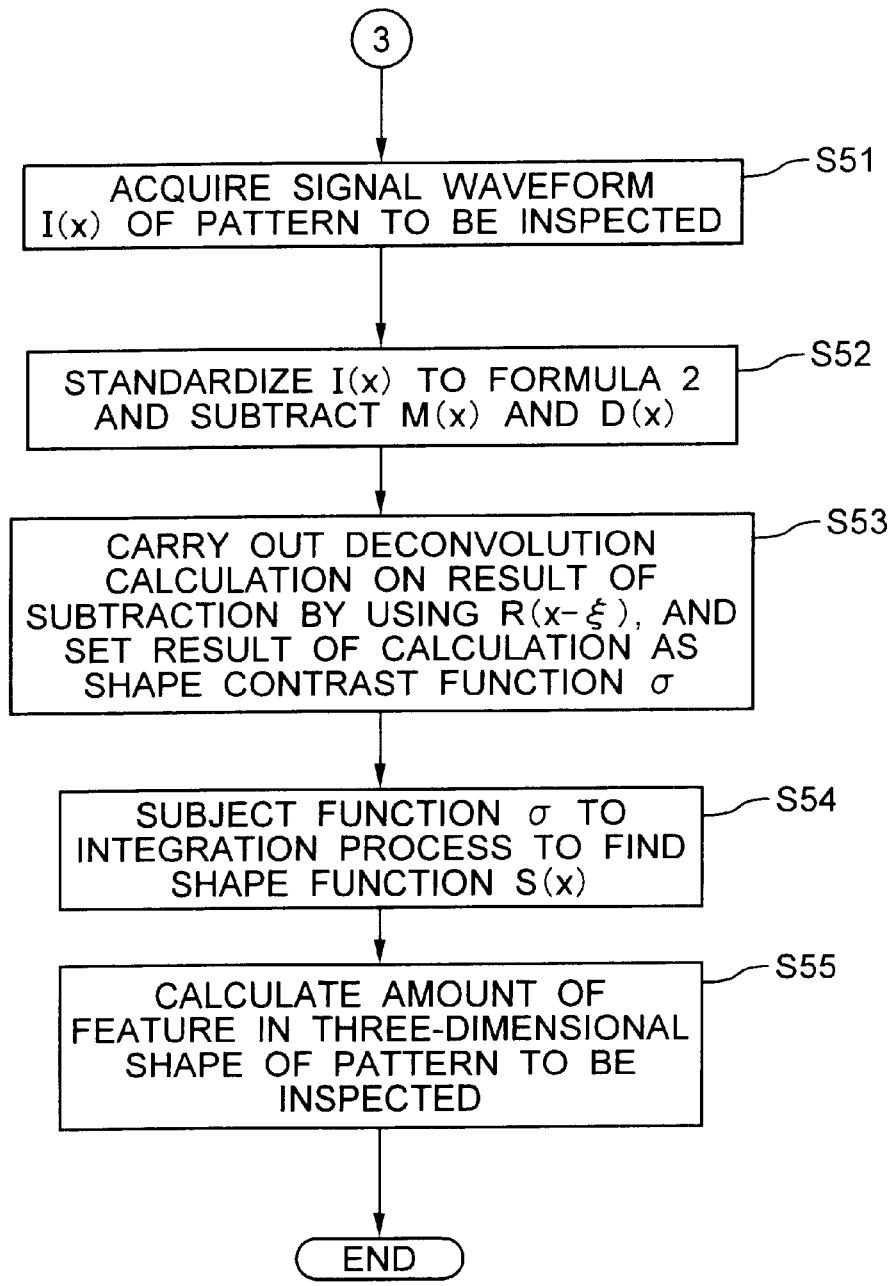

Next, referring to FIGS. 10 through 12, the following description will discuss a third embodiment of a fine pattern inspection method in accordance with the present invention.

Figure 13:
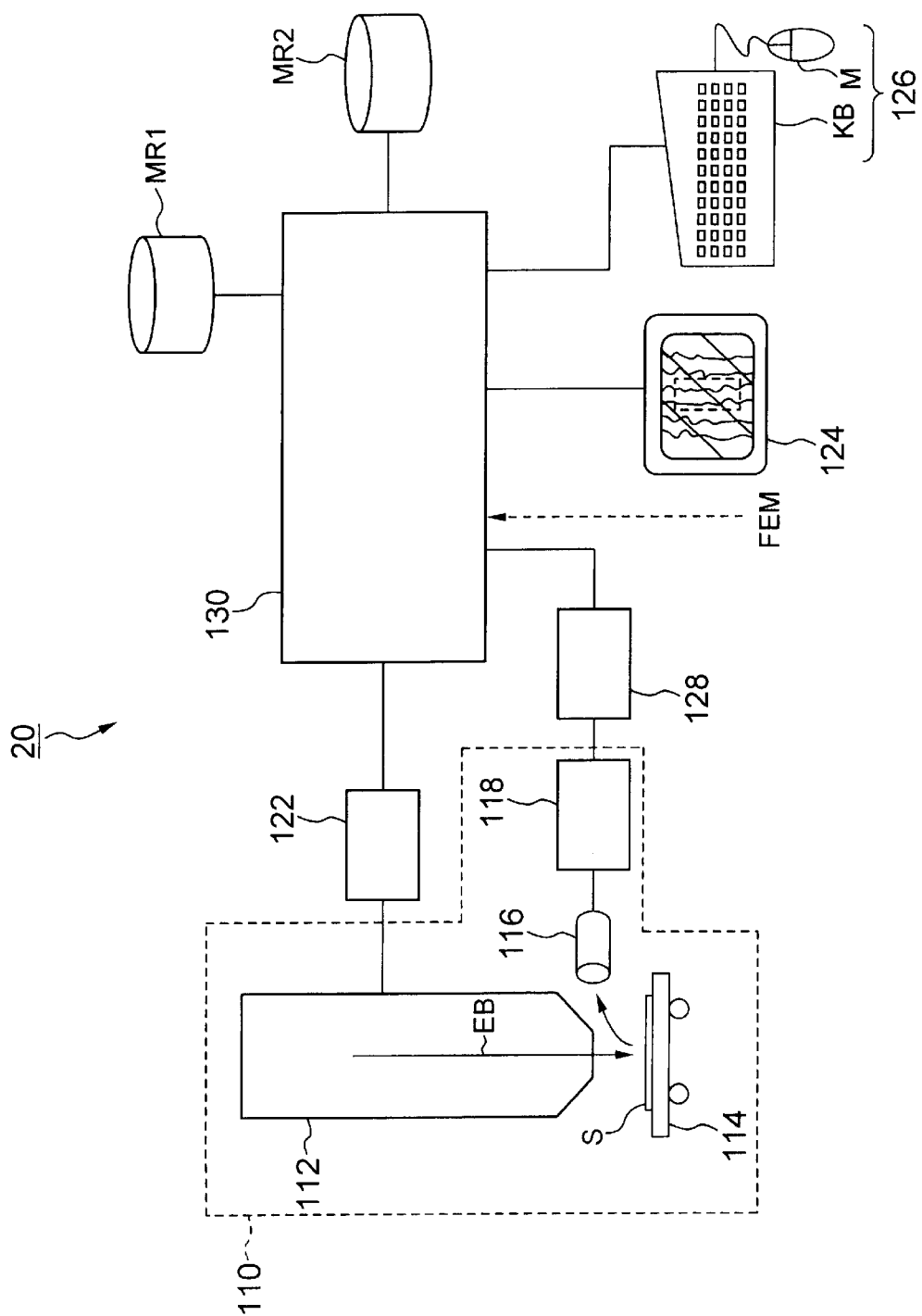
FIG. 13 is a block diagram that shows a second embodiment of a fine pattern inspection apparatus in accordance with the present invention.

FIG. 10 and FIG. 11 show a flow chart that indicates a schematic sequence of a fine pattern inspection method of the present embodiment, and FIG. 13 is an explanatory drawing that shows the fine pattern inspection method shown in FIG. 10 and FIG. 11.

As clearly be seen by comparison with FIG. 2 and FIG. 3, in the present embodiment, the sequence of steps S41 through S53 from the step of the formation of a test wafer to the step of the obtaining of a shape contrast function σ after acquiring the signal response function is substantially the same as that of the first embodiment, and each of the numbers of the steps corresponds to that added by 40. Therefore, in the following description, an explanation will start at step S54 that is a featured sequence of the present embodiment.

At step S54, a shape function S(x) is calculated by numerically integrating the function σ by using formula 3.

Next, amounts of feature in the three-dimensional shape of a pattern to be inspected are calculated (step S55). Here, in addition to the film thickness H of the pattern to be inspected, the amounts of feature of the three-dimensional shape include an amount ΔT that indicates the degree of rounding of the top edge, the curvature radius R of the top portion, an amount ΔB that indicates the degree of trailing of the bottom edge portion, a height Δh of the trailing portion, a taper angle of the wide wall θt and the presence or absence of a standing wave. Referring to FIG. 12, the following description will discuss a calculation method of these amounts of feature in detail.

Figure 12A:
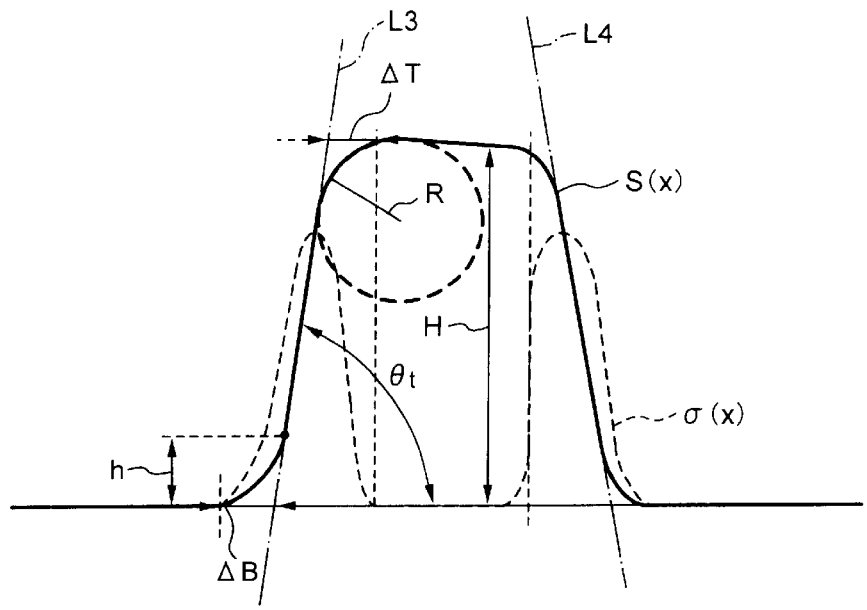
FIGS. 12A and 12B are explanatory drawings that show the fine pattern inspection method of FIGS. 10 and 11.
Figure 12B:
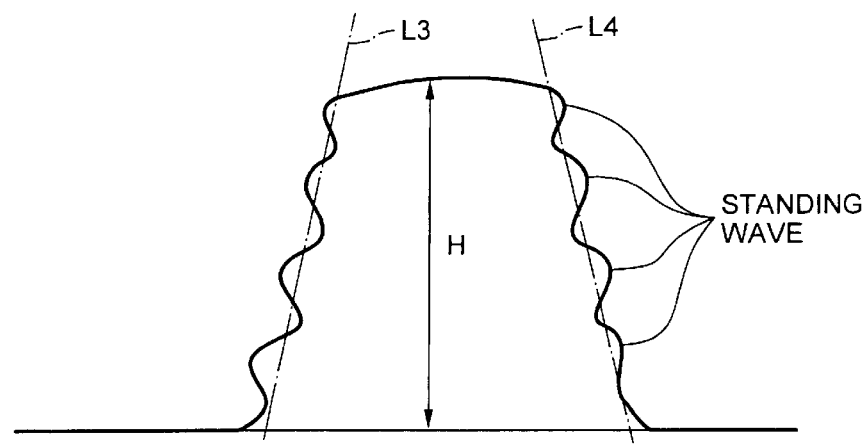

First, as shown in FIG. 12A and FIG. 12B, with respect to the shape function S(x) of a pattern to be inspected, the contour of the pattern edge portion is approximated to two straight lines L3, L4. As shown in FIG. 12A, when the contour of the pattern edge portion has only small deviations to the two straight lines L3, L4, it is determined that no standing wave exists. In contrast, as shown in FIG. 12B, the contour of the pattern edge portion has great deviations to the respective two straight lines L3, L4, it is determined that there is a standing wave. The film thickness H, ΔT, the curvature radius R, ΔB, Δh and the taper angle θt are defined as shown in FIG. 12A.

In the conventional technique, the above-mentioned three-dimensional shape, which gives effects to the etching process, has been evaluated independently from the pattern dimensional measurements, through cross-sectional observations by subjecting the cross-section of the pattern to cleavage, or by using an AFM. However, the present embodiment makes it possible to quantitatively determine such a three-dimensional shape simultaneously upon measuring the length of the pattern dimension.

(5) Second Embodiment of a Fine Pattern Inspection Apparatus

Next, referring to FIG. 13, the following description will discuss a second embodiment of a fine pattern inspection apparatus in accordance with the present invention. This Figure is a block diagram that shows a fine pattern inspection apparatus 20 of the present embodiment. As clearly be seen by comparison with the fine pattern inspection apparatus 10 shown in FIG. 1, the fine pattern inspection apparatus 20 is further comprises a de-convolution arithmetic circuit 128 that is connected to the signal processing unit 118 of the CD-SEM device 110 and the computer 130. In the above-mentioned first embodiment, the computer 120 executes de-convolution calculations. However, in the present embodiment, the exclusively-used arithmetic circuit 128 executes various de-convolution calculations. The structure of the computer 130 is substantially the same as the computer 120 shown in FIG. 1, except that it does not execute de-convolution calculations.

In addition, the other structures of the fine pattern inspection apparatus 20 of the present embodiment are substantially the same as those of the aforementioned fine pattern inspection apparatus 10. Moreover, the operations of the fine pattern inspection apparatus 20 are substantially the same as those of the fine pattern inspection apparatus 10. Therefore, the detailed description thereof is omitted.

(6) Embodiment of a Managing Apparatus of a CD-SEM Device

Figure 14:
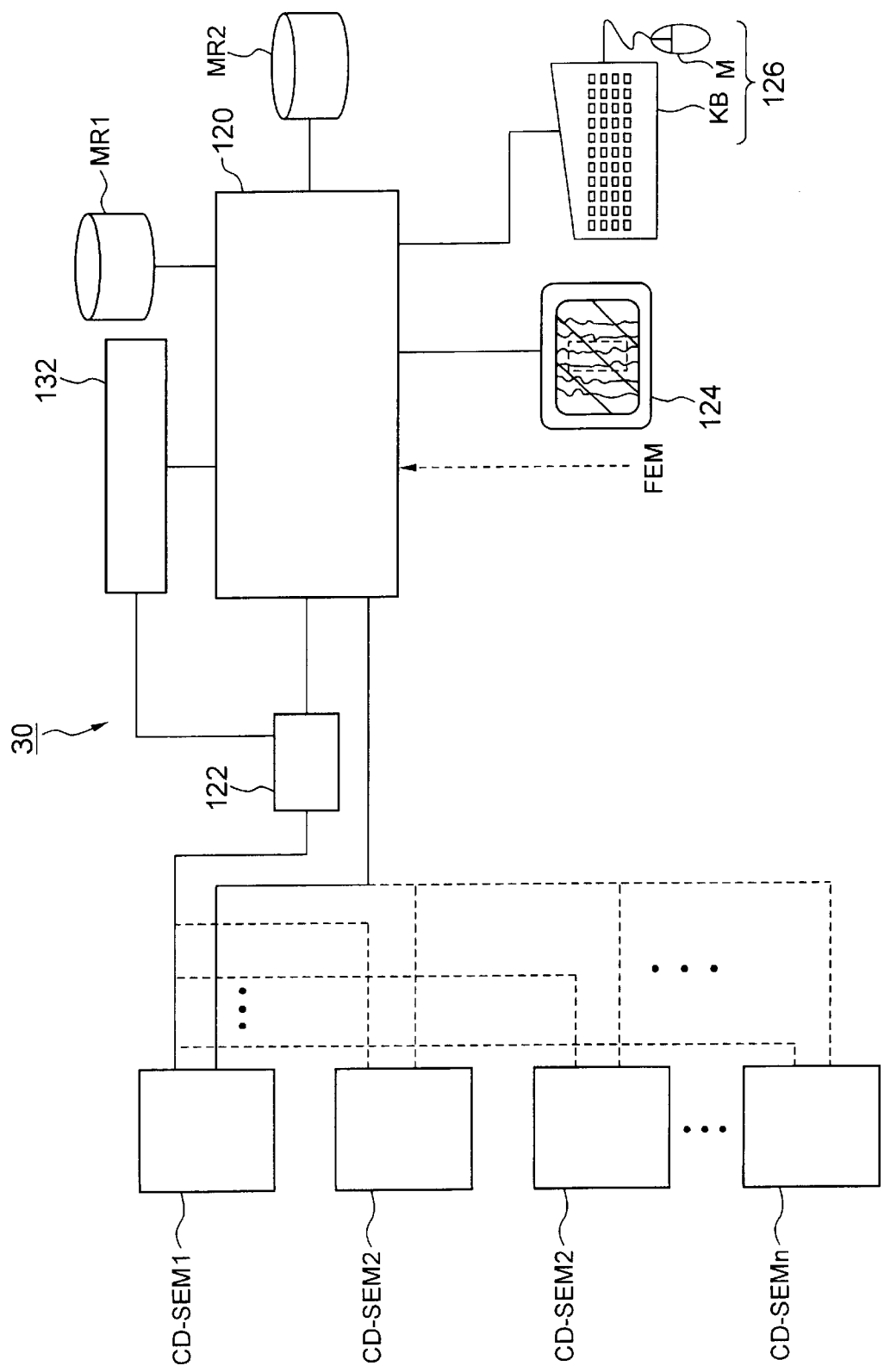
FIG. 14 is a block diagram that includes a schematic construction of an embodiment of a managing apparatus of a CD-SEM device in accordance with the present invention.

FIG. 14 is a block diagram that shows a schematic construction of one embodiment of a managing apparatus of a CD-SEM device in accordance with the present invention. In addition to the construction of the fine pattern inspection apparatus shown in FIG. 1, a managing apparatus 30 shown in FIG. 14 further comprises a CD-SEM device monitoring unit 132 connected to the computer 120 and the electronic optical system control unit 122. Recipe files in which a sequence of processes of a managing method of the CD-SEM device is written are stored in the memory MR1. The managing method of the CD-SEM device will be described later. Moreover, the computer 120 calculates shape response functions R1 through Rn of the respective CD-SEM devices 1 through n according to these recipe files, and stores the results of calculations in the memory MR2 in association with the respective calculated times. Based upon these shape response functions R1 through Rn stored in the memory MR2, the CD-SEM monitoring unit 132 monitors performance differences among the CD-SEM devices 1 through n and time-based variations in the respective CD-SEM devices themselves to supply control signals for adjusting the beam irradiation conditions and the optical system to the electronic optical system control unit 122. In the case when, as a result of the monitoring process of the time-based variations in the CD-SEM devices, there is found any CD-SEM device that fails to achieve the desired performances, the CD-SEM monitoring unit 132 also stops the operation of the corresponding device, gives a message calling for maintenance, and allows the display unit 124 to display the message through the computer 120.

The following description will discuss specific operations of the managing apparatus 30 of the CD-SEM device as an embodiment of the managing method of the CD-SEM device in accordance with the present invention.

(7) Embodiment of a Managing Method of a CD-SEM Device

First, a CD-SEM device 1 is connected to the managing apparatus 30, and after the shape contrast function $\sigma(x)$ of a test pattern and the signal response function of the CD-SEM device 1 are calculated through the sequence shown in steps S1 through S8 in FIG. 2, the shape response function of the CD-SEM device 1 is stored in the memory MR2 as R1, together with the shape contrast function $\sigma(x)$.

Next, a CD-SEM device 2, which is a device different from CD-SEM device 1, is connected to the managing apparatus 30, then the secondary electron signal of the same sample is acquired, and the above-mentioned $\sigma(x)$ is drawn from the memory MR2 so that de-convolution calculations are carried out based upon this $\sigma(x)$. Thus, a shape response function R2 is calculated from the results with respect to the CD-SEM device 2, and this function R2 is stored in the memory MR2.

In the same manner as the above-mentioned sequence, shape response functions R3, . . . Rn are found with respect to other CD-SEM devices R3 . . . Rn, and stored in the memory MR2 in association with the respective calculated times.

The CD-SEM monitoring unit 132 draws the above-mentioned results of calculations from the memory MR2, and finds the half-value width of the shape response function for each CD-SEM device, and compares the results mutually. As a result of comparisons, if there is any device having an extremely great half-value width of the shape response function, the CD-SEM monitoring unit 132 generates a control signal that sets the half-value width to a reference value with respect to the device, and supplies this control signal to the electronic optical system control unit 122 so that the beam irradiation conditions and the optical system are adjusted by using this signal.

The managing apparatus 30 further carries out the above-mentioned sequence for every predetermined time. During this period, the CD-SEM monitoring unit 132 monitors time-based variations in the half-value width of the shape response function R. As a result, if there is any CD-SEM device whose half-value width exceeds the reference value, the CD-SEM monitoring unit 132 generates a message signal calling for the stop of the operation of the corresponding device, and allows the display unit 124 to display this message so as call maintenance on the device.

In accordance with the managing method of the present embodiment, it is possible to properly control the differences in performances and time-based variations in dimensional values among the CD-SEM devices with high precision.

(8) Program and Recorded Medium

A series of procedures in the above described fine pattern inspection method may be incorporated in a program to be read by a computer to be executed. Thus, the fine pattern inspection method according to the present invention can be realized by using a general purpose computer. In addition, a program causing a computer to execute the series of procedures in the above described fine pattern inspection method may be stored in a recording medium, such as a flexible disk or a CD-ROM, to be read and executed by the computer.

Furthermore, a series of procedures in the above described managing method of the CD-SEM device may be incorporated in a program to be read by a computer to be executed, and a program causing a computer to execute the series of procedures in the above described managing method of the CD-SEM device may be stored in a recording medium, such as a flexible disk or a CD-ROM, to be read and executed by the computer. Thus, the managing method of the CD-SEM device according to the present invention can be realized by using a general purpose computer.

The recording medium should not be limited to a portable recording medium, such as a magnetic disk or an optical disk, but it may be a fixed recording medium, such as a hard disk unit or a memory. In addition, a program including the above described series of procedures in the fine pattern inspection method and/or the managing method of the CD-SEM device may be distributed via a communication line (including a radio communication), such as Internet. Moreover, a program including the series of procedures in the above described series of procedures in the fine pattern inspection method and/or the managing method of the CD-SEM device is encrypted, modulated or compressed to be distributed via a wire or radio line, such as Internet, or to be stored in a recording medium to be distributed.

While some embodiments of the present invention have been described, the invention should not be limited to the above described embodiments, and persons with ordinary skill in the art can modify the invention in various ways without departing from the spirit of the invention.

What is claimed is:

1. A fine pattern inspection apparatus comprising:
   a first calculation unit which receives data of a first secondary electron signal obtained by irradiating a plurality of test patterns formed on a test substrate with an electron beam and receives data of a contour shape of a cross-section of each of the test patterns, the test substrate being the same as a substrate on which a pattern to be inspected is formed, the test patterns being formed with different cross-sectional shapes, and which separates said first secondary electron signal into variables of a first function containing the contour shape of the cross-section as arguments, a second function that is defined by a step function depending on respective materials constituting the test patterns and a third function that represents the size of a distortion of the signal;
   a storing unit which has a first storing area to store said first through third functions obtained from said first calculation unit; and a second calculation unit which receives data of a second secondary electron signal obtained by irradiating the pattern to be inspected with an electron beam, and executes calculations so as to extract components relating to the cross-sectional shape of the pattern to be inspected from said second secondary electron signal by using said first through third functions stored in said storing unit.

2. A fine pattern inspection apparatus according to claim 1, further comprising:

a third calculation unit which calculates an inversion function of said first function obtained by said first calculation unit, wherein said storing unit further comprises a second storing area that stores said inversion function as a digital filter, and said second calculation unit draws said second and third functions from said first storing area of said storing unit, and subtracts components of said second and third functions from said second secondary electron signal so that components relating to the cross-sectional shape of the pattern to be inspected are extracted by applying said digital filter to the results of the subtraction.

3. A fine pattern inspection apparatus according to claim 1, wherein said second calculation unit further calculates an amount of feature of the three-dimensional shape of the pattern to be inspected on the basis of said extracted components relating to the cross-sectional shape of the pattern to be inspected.

4. A fine pattern inspection apparatus according to claim 3, wherein said amount of feature includes at least one of the factors including a film thickness of the pattern to be inspected, an amount of a shape change in the vicinity of a top edge, a curvature radius of a top portion, an amount of a shape change in the vicinity of a bottom edge, a height of a trailing portion, a taper angle of a side wall and the presence or absence of a standing wave in the side wall.

5. An apparatus connectable to CD-SEM devices and which manages the Critical Dimension—Scanning Electron Microscope devices, said managing apparatus comprising:

a calculation unit which receives data of a secondary electron signal from a plurality of different CD-SEM devices and receives data of an contour shape of a cross-section of each of the test patterns, the secondary electron signal being obtained by irradiating a plurality of test patterns formed on a test substrate with an electron beam, the test substrate being the same as a substrate on which a pattern to be inspected is formed, the test pattern being formed with different cross-sectional shapes, and which separates said secondary electron signal into variables of a first function containing said contour shape of the cross-section as arguments, a second function that is defined by a step function depending on respective materials constituting the test patterns and a third function that represents the size of a distortion of the signal, for each of the CD-SEM devices;

a storing unit which stores said first function obtained from said calculation unit for each of the CD-SEM devices; and a monitoring unit which monitors performance differences among the CD-SEM devices by mutually comparing said first functions among the CD-SEM devices.

6. An apparatus according to claim 5, wherein said calculation unit respectively receives said data of the secondary electron signal from the CD-SEM devices at different times, and separates said secondary electron signal to variables of said first through third functions for each of the CD-SEM devices and for each of said times, said storing unit stores said first function obtained from said calculation unit in association with combinations of the respective CD-SEM devices and the respective times, and said monitoring unit monitors the performance differences and the time-based variations among the CD-SEM devices by comparing said first functions among the CD-SEM devices as well as among said times.

7. An apparatus connectable to a CD-SEM device and which manages the CD-SEM device, said managing apparatus comprising:

a calculation unit which receives data of a secondary electron signal from the CD-SEM device at different times and receives data of an contour shape of a cross-section of each of the test patterns, the secondary electron signal being obtained by irradiating a plurality of test patterns with an electron beam, the test patterns being formed on a substrate with different cross-sectional shapes, and which separates said secondary electron signal into variables of a first function containing said contour shape of the cross-section as arguments, a second function that is defined by a step function depending on respective materials constituting the test patterns and a third function that represents the size of a distortion of the signal, at each of the times;

a storing unit which stores said first function obtained from said calculation unit in association with each of said times; and a monitoring unit which monitors time-based variations in the CD-SEM devices by mutually comparing said first functions among said times.

8. A fine pattern inspection method comprising:

acquiring data of a first secondary electron signal obtained by irradiating a plurality of test patterns formed on a test substrate with an electron beam, the test substrate being the same as a substrate on which a pattern to be inspected is formed, the test patterns being formed with different cross-sectional shapes, and acquiring data of an contour shape of a cross-section of each of the test patterns;

separating said first secondary electron signal into variables of a first function containing said contour shape of the cross-section as arguments, a second function that is defined by a step function depending on respective materials constituting the test patterns and a third function that represents the size of a distortion of the signal;

recording said first through third functions obtained from said separation of variables;

acquiring data of a second secondary electron signal obtained by irradiating the pattern to be inspected with an electron beam; and executing calculations so as to extract components relating to the cross-sectional shape of the pattern to be inspected from said second secondary electron signal by using said first through third functions that have been recorded.

9. A fine pattern inspection method according to claim 8, further comprising:

calculating an inversion function of said first function obtained through said separation of variables; and storing said inversion function as a digital filter, wherein
said components relating to the cross-sectional shape of the pattern to be inspected are extracted by subtracting components of said second and third functions from said second secondary electron signal and applying said digital filter to the results of the subtraction.

10. A fine pattern inspection method according to claim 8, further comprising calculating an amount of feature of the three-dimensional shape of the pattern to be inspected on the basis of said components relating to the cross-sectional shape of the pattern to be inspected.

11. A fine pattern inspection method according to claim 10, wherein
said amount of feature includes at least one of the factors including a film thickness of the pattern to be inspected, an amount of a shape change in the vicinity of a top edge, a curvature radius of a top portion, an amount of a shape change in the vicinity of a bottom edge, a height of a trailing portion, a taper angle of a side wall and the presence or absence of a standing wave in the side wall.

12. A managing method of a CD-SEM device comprising:
acquiring data of a secondary electron signal from a plurality of different CD-SEM devices, the secondary electron signal being obtained by irradiating a plurality of test patterns with an electron beam, the test patterns being formed on a substrate with different cross-sectional shapes;
acquiring data of a contour shape of a cross-section of each of the test patterns;
separating said secondary electron signal into variables of a first function containing said contour shape of the cross-section as arguments, a second function that is defined by a step function depending on respective materials constituting the test patterns and a third function that represents the size of a distortion of the signal, for each of the CD-SEM devices;
recording said first function for each of the CD-SEM devices; and
monitoring performance differences among the CD-SEM devices by mutually comparing said first functions among the CD-SEM devices.

13. A managing method of a CD-SEM device according to claim 12, wherein
said data of the secondary electron signal are acquired from the CD-SEM devices at different times,
said secondary electron signal is separated to variables of said first through third functions for each of the CD-SEM devices and for each of said times,
said first function obtained through said separation of variables is stored in association with combinations of the respective CD-SEM devices and the respective times, and
said monitoring the performance differences includes comparing said first functions among the CD-SEM devices as well as among said times so that the performance differences and time-based variations among the CD-SEM devices are monitored.

14. A managing method of a CD-SEM device comprising:
acquiring data of a secondary electron signal from the CD-SEM device at different times, the secondary electron signal being obtained by irradiating a plurality of test patterns with an electron beam, the test patterns being formed on a substrate with different cross-sectional shapes;
acquiring data of a contour shape of a cross-section of each of the test patterns;
separating said secondary electron signal into variables of a first function containing said contour shape of the cross-section as arguments, a second function that is defined by a step function depending on respective materials constituting the test patterns and a third function that represents the size of a distortion of the signal, at each of the times;
recording said first function obtained from said separation of variables in association with each of said times; and
monitoring time-based variations in the CD-SEM devices by mutually comparing said first functions among said times.

15. A program which allows a computer to execute a fine pattern inspection method comprising:
acquiring data of a first secondary electron signal obtained by irradiating a plurality of test patterns formed on a test substrate with an electron beam, the test substrate being the same as a substrate on which a pattern to be inspected is formed, the test patterns being formed with different cross-sectional shapes, and acquiring data of an contour shape of a cross-section of each of the test patterns;
separating said first secondary electron signal into variables of a first function containing said contour shape of the cross-section as arguments, a second function that is defined by a step function depending on respective materials constituting the test patterns and a third function that represents the size of a distortion of the signal;
recording said first through third functions obtained from said separation of variables;
acquiring data of a second secondary electron signal obtained by irradiating the pattern to be inspected with an electron beam; and
executing calculations so as to extract components relating to the cross-sectional shape of the pattern to be inspected from said second secondary electron signal by using said first through third functions that have been recorded.

16. A program which allows a computer to execute a managing method of a CD-SEM device comprising:
acquiring data of a secondary electron signal from a plurality of different CD-SEM devices, the secondary electron signal being obtained by irradiating a plurality of test patterns with an electron beam, the test patterns being formed on a substrate with different cross-sectional shapes;
acquiring data of a contour shape of a cross-section of each of the test patterns;
separating said secondary electron signal into variables of a first function containing said contour shape of the cross-section as arguments, a second function that is defined by a step function depending on respective materials constituting the test patterns and a third function that represents the size of a distortion of the signal, for each of the CD-SEM devices;
recording said first function for each of the CD-SEM devices; and
monitoring performance differences among the CD-SEM devices by mutually comparing said first functions among the CD-SEM devices.

17. A program which allows a computer to execute a managing method of a CD-SEM device comprising:
acquiring data of a secondary electron signal from the CD-SEM device at different times, the secondary electron signal being obtained by irradiating a plurality of test patterns with an electron beam, the test patterns being formed on a substrate with different cross-sectional shapes;

acquiring data of a contour shape of a cross-section of each of the test patterns;

separating said secondary electron signal into variables of a first function containing said contour shape of the cross-section as arguments, a second function that is defined by a step function depending on respective materials constituting the test patterns and a third function that represents the size of a distortion of the signal, at each of the times;

recording said first function obtained from said separation of variables in association with each of said times; and monitoring time-based variations in the CD-SEM devices by mutually comparing said first functions among said times.

* * * * *

UNITED STATES PATENT AND TRADEMARK OFFICE
CERTIFICATE OF CORRECTION

PATENT NO. : 6,642,519 B2
DATED : November 4, 2003
INVENTOR(S) : Ikeda

It is certified that error appears in the above-identified patent and that said Letters Patent is hereby corrected as shown below:

Title page,
Item [57], ABSTRACT,
Line 5, change "an contour" to -- a contour --.

Column 15,
Line 44, change "an contour" to -- a contour --.

Column 16,
Line 19, change "an contour" to -- a contour --.
Line 45, change "an contour" to -- a contour --.

Column 18,
Line 22, change "an contour" to -- a contour --.

Signed and Sealed this

Thirteenth Day of January, 2004

JON W. DUDAS
*Acting Director of the United States Patent and Trademark Office*